United States Patent [19]

Andersson

[11] 4,438,163
[45] Mar. 20, 1984

[54] PAD WITH SHAPE ADAPTING PROPERTIES

[75] Inventor: Karl G. B. Andersson, Halmstad, Sweden

[73] Assignee: Duni Bila AB, Halmstad, Sweden

[21] Appl. No.: 268,082

[22] Filed: May 28, 1981

[30] Foreign Application Priority Data

May 30, 1980 [SE] Sweden .............................. 8004063

[51] Int. Cl.$^3$ ............................................. B32B 23/02
[52] U.S. Cl. ...................................... 428/35; 181/129; 428/40; 428/131; 428/194
[58] Field of Search ................. 428/14, 133, 40, 35, 428/131; 128/132 R, 150, 151, 152, 163, 481, 505; 2/174, 209; 181/129; D2/24; 248/459

[56] References Cited

U.S. PATENT DOCUMENTS

| D. 75,292 | 5/1928 | Schleicher | 428/14 X |
|---|---|---|---|
| 2,120,456 | 6/1938 | Barnes | 428/14 X |
| 2,159,435 | 5/1939 | Gribbin | 2/174 |
| 2,633,440 | 3/1953 | Scholl | 128/505 X |
| 3,601,493 | 8/1971 | Levy | 248/206 X |
| 3,741,079 | 6/1973 | Bossons et al. | 428/133 X |
| 3,846,218 | 11/1974 | Wootten | 428/133 X |
| 3,949,137 | 4/1976 | Akrongold et al. | 427/244 X |

FOREIGN PATENT DOCUMENTS 141169  5/1951  Australia ............................ 428/133

Primary Examiner—Marion McCamish
Attorney, Agent, or Firm—Holman & Stern

[57] ABSTRACT

A pad with shape adapting properties, including at least two adjacently located layers of a preferably absorbing material which are joined together in the region of the outer peripheral edge portions of the layers the layers further including a free tongue-shaped portion extending in an overlapping relationship to corresponding parts in remaining layers, the overlapping tongue-shaped parts being arranged to glide or slide in relation to each other to an overlapping position with the line of extension adapted to the configuration of an object covered by the tongue-shaped parts. Opposed portions of the layers defined by cuts surrounding the tongue-shaped portions, are also preferably arranged to act as shape adaptable parts, co-acting with the tongue-shaped parts.

16 Claims, 7 Drawing Figures

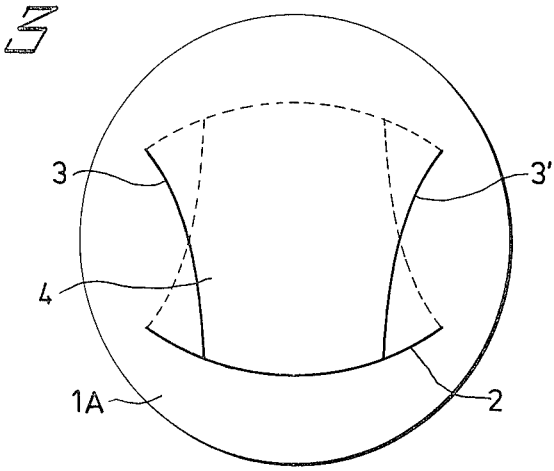
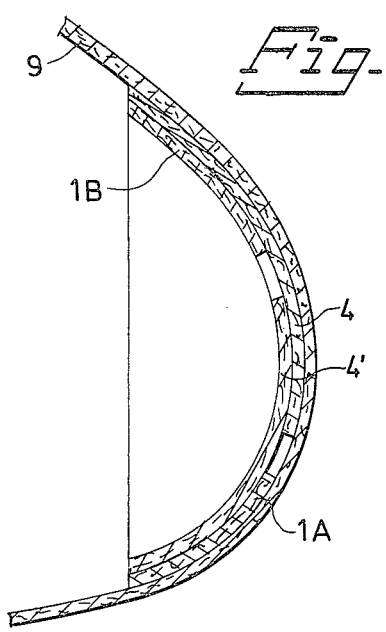

4,438,163

PAD WITH SHAPE ADAPTING PROPERTIES

BACKGROUND OF THE INVENTION

1. Field of the Invention

The present invention relates to a pad with shape adapting properties, and preferably a moisture or liquid absorbing pad.

2. Description of the Prior Art

There is a need for pads with shape adapting properties in various fields of use, e.g. breast shields, made from an absorbing material. Most pads which are currently available have been shaped into desired configuration when manufactured. The shape established when manufactured can thus not be changed by the user, and as a result, the shape can not be adapted to the requirements of each individual user. Furthermore such pre-shaped pads are also difficult to provide in pocket-size packages due to the manufactured configuration, and are also difficult to dispense from table or wall dispensers.

SUMMARY OF THE INVENTION

The object of the present invention is to provide a pad with shape adapting properties, which prior to use extends in one plane only, and which does not exert pressure on a protruding object protected by the pad, and also protects said object from touching or contacting other objects applied in direction towards the pad. These features have been unobtainable with previously known techniques, and it is now possible to supply plane pads with shape adapting properties, which efficiently protect and adapt to the configuration of the object to be protected, and such an individual adaption has been impossible to achieve with pre-shaped pads.

The pad with shape adapting properties according to the present invention is mainly characterised in that it includes at least two adjacently located layers of a preferably absorbing material, each layer including a free tongue-shaped part arranged extending in in an overlapping relationship to each other, arranged to faciliate a sliding or gliding movement in relation to each other to an overlapping position, in which the line of extension corresponds to the configuration of an object surrounded by the tongue-shaped parts.

A number of embodiments of pads with shape adapting properties according to the present invention are more fully described below, reference being made to the accompanying drawings.

BRIEF DESCRIPTION OF THE DRAWINGS

FIG. 1 is a plan view of a first embodiment of a pad with shape adapting properties according to the present invention, intended to be applied against an ear-conch of a hearing-shield or similar.

FIG. 3 is a plan view of a breast shield before it is applied against a human breast in a brassiere.

FIG. 4 is a cross-sectional view of a brassiere with the breast shield shown in FIG. 3 applied.

DESCRIPTION OF THE PREFERRED EMBODIMENTS

Figure 1:
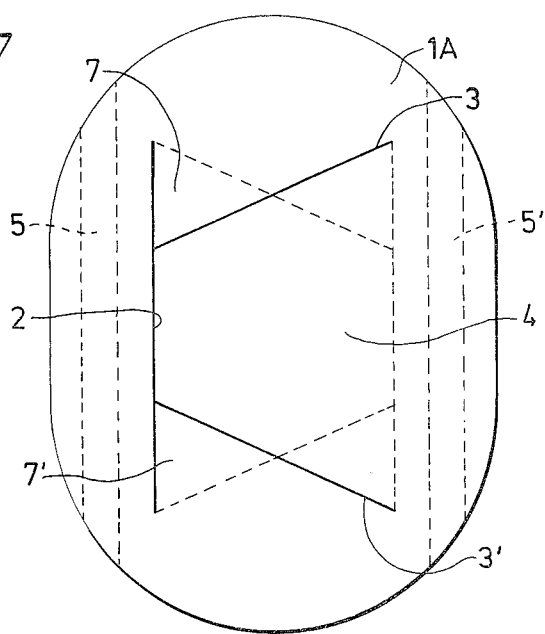
Figure 2:
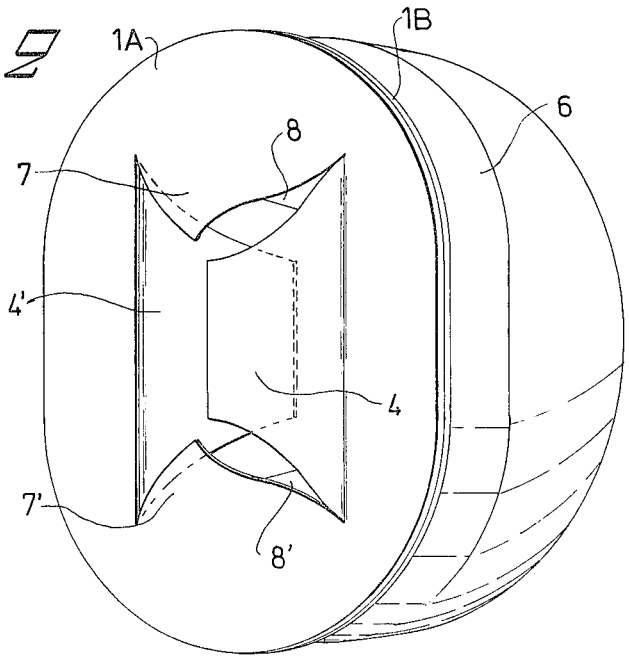
FIG. 2 is a perspective view of an ear-conch with the pad shown in FIG. 1 applied, after that the ear-conch has been placed in a position to surround an ear, and thereafter been removed.

With reference to the embodiment shown in FIGS. 1 and 2, it comprises two adjacently located layers of a plane absorbing material, denominated 1A and 1B respectively. Said two layers 1A, 1B, in relation to each other as two reversed parts, both including a first cut 2 extending adjacent to an outer edge portion, and two edge cuts 3, 3' extending from said first cut at a distance from each other, said first cut 2 and the edge cuts 3, 3' forming a tongue-shaped part, 4 and 4', respectively. Two strips of a self-adhesive material, 5 and 5', are also shown in FIG. 1, located at the surface of the pad intended to contact an ear-conch 6. The self-adhesive strips 5, 5' are protected before application by means of a protective tape or similar.

The adjacently located layers 1A, 1B are joined together at the surrounding outer edge portions, whereby the tongue-shaped parts 4, 4' are arranged to permit a sliding or gliding movement in relation to each other, when a pressure is applied against same.

When used, the protective tape is removed from the self-adhesive strips 5, 5', whereafter the plane pad is applied against the outer free surface of an ear-conch 6. When said ear-conch is applied in a position surrounding an ear, the insertion of the ear into the ear-conch 6 causes the tongues 4, 4' to perform a sliding or gliding movement in relation to each other, in order to adapt to the shape of the ear. Since the edge cuts 3, 3' are arranged extending from the first cut 2 from two points located more adjacent to each other than the outer end points of the first cut 2, having the opposed end points located separated from each other at a distance mainly corresponding to the length of the first cut 2, two mainly triangular parts 7, 7' and 8, 8' respectively, are formed adjacent to each tongue-shaped part 4, 4'. When the ear is inserted into the ear-conch 6, said triangular parts 7, 7', 8, 8' are folded in direction inwardly into the ear-conch 6, thereby forming two opposed wall portions, which together with the tongue-shaped parts 4, 4' effectively shield and protect the inside of the ear-conch 6. An important advantage is, that the parts 4, 4', 7, 7', 8, 8', adapted to the shape of the ear, do not prevent or, to any larger extent, restrict sound waves from an earpiece, surrounded by the ear-conch 6, whereby said embodiment is eminently suitable for use as a pad with shape adapting properties for ear-phones used in connection with radio or sound equipment.

With reference to the embodiment shown in FIGS. 3 and 4 of a breast shield, the reference numerals used with regard to the embodiment described with reference to FIGS. 1 and 2 have been used to denominate parts with a similar function. The breast shield shown comprises two adjacently located layers 1A, 1B of a plane and absorbing material, joined together at the surrounding outer edge portions. In order to faciliate adaption to the internal concave shape of a brassiere 9, said adjacently located layers 1A, 1B have a mainly circular outer configuration. As discussed with reference to the first embodiment, said layers 1A, 1B also include correspondingly cut out tongue-shaped parts 4, 4', located rotated 180° in relation to each other. The first cut 2 is arranged as a peripherally located curved cut, having a radius preferably exceeding the outer radius of the layers 1A, 1B. The edge cuts 3, 3' are also arranged curved, extending from two points at the first cut 2 located at a distance from the outer end portions of said cut 2, and extending to two points mainly corresponding to the end portions of a first cut in the adjacent layer, 1A or 1B. By arranging said cuts 2, 3, 3' curved as disclosed above, a breast shield is accomplished, which faciliates complete adaption to the shape of the body of each user, since the tongue-shaped parts 4, 4' when applied slide in relation to each other, whereby shape adaption for each application is achieved. A major advantage is, that the breast shield can be carried as a plane unit prior to use, and that it completely adapts to existing variations in shape and size of the bosom when applied.

Figure 5:
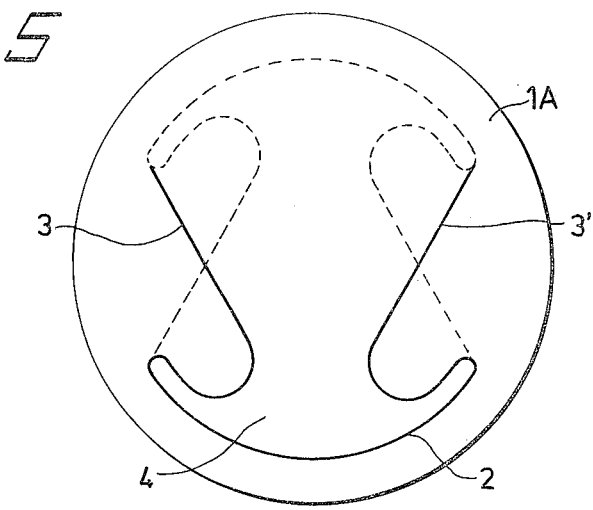
FIG. 5 is a plan view of an embodiment, suitably used as a head shield in conjunction with a protective helmet.

A further embodiment is shown in FIG. 5, intended to be used as a head shield, e.g. together with a protective helmet. Previously used reference numerals have been used to denominate parts with a function basically similar to the embodiments already descussed. The head shield comprises two layers 1A, 1B, joined together at the surrounding outer edge portions. As disclosed with reference to the breast shield, the head shield has a mainly circular configuration, having correspondingly cut out parts, rotated 180° in relation to each other. In view of the fact that the head is inserted a rather long distance into the helmet, the first cut 2 is located rather adjacent to the outer peripheral portion of the joined layers 1A, 1B, and the peripheral portions located on each side of the edge cuts 3, 3' are well suited to extend downwardly from the helmet, thus acting as protective shields for the ears of the user.

Figure 6:
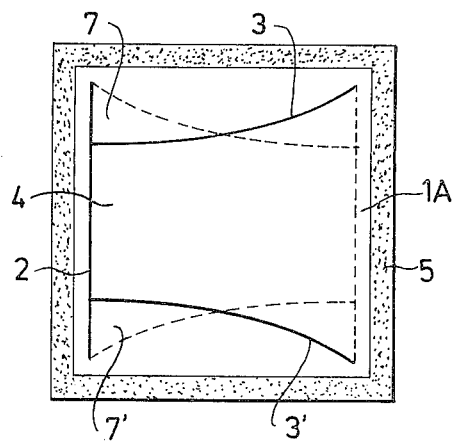
FIG. 6 is a plan view of an embodiment, preferably used as a protective dressing, viewed from the surface of application.

FIG. 6 discloses a further embodiment, intended to be used as a protective dressing. Said embodiment includes also two adjacently located layers 1A, 1B of a preferably absorbing material, joined together at the outer edge portions, and having tongue-shaped parts 4, 4', rotated 180° in relation to each other. Each layer 1A, 1B is arranged with a first cut 2, located adjacent to one edge portion, defining a free edge portion of the tongue-shaped parts 4, 4', which are further defined by means of two curved edge cuts 3, 3', extending basically as discussed previously with reference to the embodiment of a breast shield. The protective dressing also includes a surrounding strip of self-adhesive material 5, preferably protected by means of a protective tape or film, which when removed facilitates application to a body member to cover the surface of a wound, intended to be protected by the dressing. Since the tongue-shaped parts 4, 4' can glide or slide in relation to each other, they do not inflict any pressure on the surface of the wound, but efficiently shield same.

Figure 7:
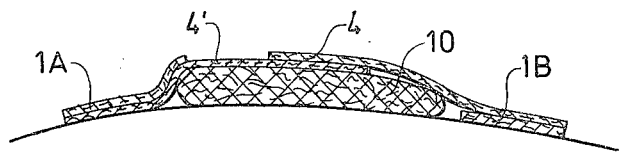
FIG. 7 is a cross-sectional view of the embodiment shown in FIG. 6 arranged at the surface of a wound together with a removable compress.

The above disclosed embodiment may also be used together with an absorbing compress or pad 10, e.g. for skin burns. An example of this is shown in FIG. 7, in which the protective dressing shown in FIG. 6 it utilized to hold a compress or pad 10, applied against the surface of a wound. In order to completely secure the compress or pad 10, the tongue-shaped parts 4, 4' may be sealed to prevent an opening movement by means of a tape or similar. The compress can be easily replaced by folding the tongue-shaped parts 4, 4' in a direction opposite to each other to an open position, and after replacement they are folded back to the previous overlapping position, thereafter possibly sealed together as previously disclosed.

All the above described embodiments are based on the use of two correspondingly formed layers 1A, 1B, joined together at said layers 1A, 1B outer edge portions. However, for certain applications, the number of layers may exceed two, e.g. four corresponding layers in contact with each other, located rotated 90° in relation to each other. Such an embodiment makes it possible to shield the surface to be protected in a better fashion, while maintaining minimum contact pressure against the shielded surface. The number of layers 1A, 1B may be varied further, with adjacent layers 1A, 1B preferably rotated to each other at an angle corresponding to 360° divided by said number.

It should also be emphasized, that pads with shape adapting properties according to the present invention obviously can be used for numerous other applications than the applications shown and described as examples of field of use. As examples of further applications can be mentioned suspender shields, and also the possibility to accomplish sun protective head wear, as well as other articles for which shape adapting properties are desired or necessary.

The embodiments shown and described also include correspondingly cut layers 1A, 1B, but certain differences may be desired with regard to the shape of the tongue-shaped parts 4, 4' for certain applications. The angle by which adjacent layers 1A, 1B are rotated in relation to each other can also be varied within broad limits, while maintaining an overlapping relationship between the tongue-shaped parts 4, 4'.

The present invention is thus in no way restricted to the embodiments shown and described, which only serve as examples of embodiments within the scope of the inventive thought and the following claims.

I claim:

1. A configuration conforming pad comprising at least two adjacently located superposed layers of flexible material, joined together at the surrounding outer edge portions thereof, each of the layers including an attached tongue-shaped flap defined by cuts in the layer from which it is formed, said tongue-shaped flaps being disposed in overlapping relationship and adapted to be folded out of the plane of their respective layers along the line of attachment and slideably and overlappingly repositioned to substantially surround and conform to an object placed in the pad.

2. The configuration conforming pad according to claim 1, wherein said material is an absorbing material.

3. The configuration conforming pad according to claim 1, wherein at least one external layer of said pad has at least one adhesive strip located thereon.

4. The configuration conforming pad according to claim 3, wherein said at least one adhesive strip is self-adhesive.

5. The configuration conforming pad according to claim 4, wherein said at least one self-adhesive strip has a removable protective layer placed thereon.

6. The configuration conforming pad according to claim 1, wherein each of said at least two layers is joined to the next adjacent layer at at least one outer peripheral portion of each layer.

7. The configuration conforming pad according to claim 1, wherein the number of layers is at least three and the angle formed between lines extending through each line of attachment in adjacent layers is 360°/number of layers.

8. The invention of claim 1, wherein each of the tongue-shaped flaps is defined by a first cut opposite the line of attachment and two side cuts each extending from an intersection with the first cut to respective end points, which define the line of attachment.

9. The invention of claim 8, wherein the first cut of each tongue-shaped flap is aligned with the line of attachment of the tongue-shaped flap in the next adjacent layer of the pad.

10. The invention of claim 8, wherein the first cut of each of the tongue-shaped flaps extends beyond the intersections with the respective side cuts so that the end points of the side cuts and the end points of the first cut define lines of attachment for third and fourth flaps in each layer.

11. The invention of claim 8, wherein the first cut extends only between the intersections with the side cuts.

12. The invention of claim 8, wherein each layer includes one tongue-shaped flap.

13. The invention of claim 12, wherein the tongue-shaped flaps in each layer are substantially congruent, and are disposed in a 180° relationship in adjacent layers.

14. The configuration conforming pad according to claim 8, wherein at least one of the cuts is curved.

15. The configuration conforming pad according to claim 8, wherein at least one of the cuts is linear.

16. The invention of claim 1, wherein the pad comprises two layers.

* * * * *